(12) United States Patent
Linev

(10) Patent No.: US 7,940,890 B1
(45) Date of Patent: May 10, 2011

(54) DIGITAL MAMMOGRAPHY SCANNING SYSTEM

(75) Inventor: Vladimir N. Linev, Minsk (BY)

(73) Assignee: Adani, Minsk (BY)

( * ) Notice: Subject to any disclaimer, the term of this patent is extended or adjusted under 35 U.S.C. 154(b) by 105 days.

(21) Appl. No.: 12/503,171

(22) Filed: Jul. 15, 2009

(51) Int. Cl.
*A61B 6/04* (2006.01)
(52) U.S. Cl. .......................... 378/37; 378/146; 378/196
(58) Field of Classification Search .................... 378/37, 378/62, 146, 189, 193, 195, 196, 197
See application file for complete search history.

(56) References Cited

U.S. PATENT DOCUMENTS 5,917,881 A * 6/1999 Jeffery ......................... 378/98.8

* cited by examiner

*Primary Examiner* — Jurie Yun
(74) *Attorney, Agent, or Firm* — Bardmesser Law Group

(57) ABSTRACT

An apparatus for use in imaging an area of interest within a patient's body, including a stationary frame; a rotating assembly mounted on the stationary frame, the rotating assembly including an axle assembly having a substantially horizontal axis of rotation, an X-ray source having a focal spot that coincides with the horizontal axis of rotation; a collimator from which a fan-shaped X-ray beam exits towards a detector assembly, and a rotating frame mechanically coupled to the detector assembly and pivoting about the horizontal axis of rotation. The detector assembly includes a linear X-ray detector for detecting radiation of the fan-shaped X-ray beam after the beam passes through the area of interest, and is mechanically coupled to a motor that enables arcuate movement of the detector assembly in a transverse direction. The motor is mechanically coupled to the rotating assembly to enable rotational movement of the rotating assembly.

14 Claims, 11 Drawing Sheets

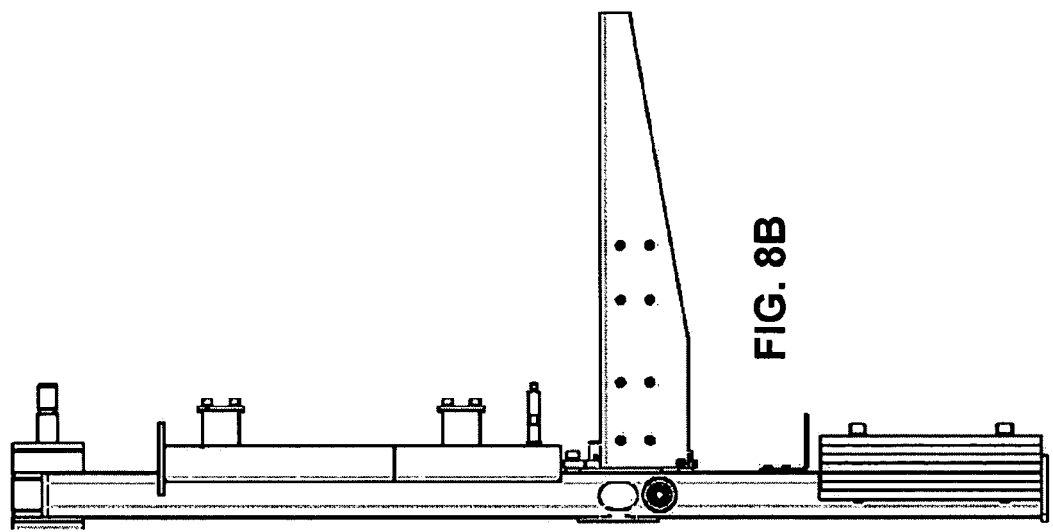
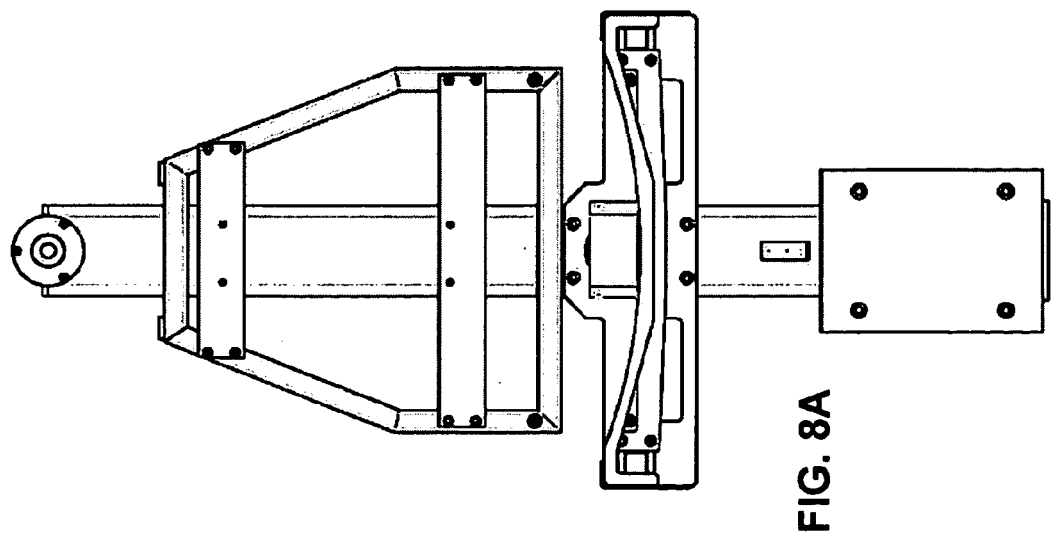

DIGITAL MAMMOGRAPHY SCANNING SYSTEM

BACKGROUND OF THE INVENTION

1. Field of the Invention

The present invention relates to full field digital mammography, in particular, to an apparatus for X-ray imaging a selected region of a patient's body by X-ray slot-scanning across the region and constructing a composite X-ray image of the region based on the scan. The invention has particular application to the field of mammography.

2. Description of the Related Art

Breast X-ray imaging is considered the most demanding of medical imaging procedures. With regard to spatial resolution, breast imaging specialists are now commonly interested in imaging lesions or masses that may require an imaging aperture that is about 50 microns in size or less. Contrast requirements are also demanding because lesions or masses to be visualized sometimes have x-ray absorption characteristics similar to that of the surrounding tissue. In this regard, 12 bit Analog to Digital Converters, which produce a contrast resolution of about 4000 distinguishable shades between black and white in the resulting image, is often found in many systems. 14-bit ADCs are also common today, and the market is moving to 16-bit ADCs, corresponding to about 65,000 shades of gray.

X-ray mammography is the most sensitive breast imaging modality currently available and is widely used in detecting and diagnosing the nature of small non-palpable breast lesions. Both film-based and digital X-ray systems are currently available for breast imaging. In film-based systems, x-rays are transmitted through the patient's breast and impinge upon a phosphor screen. Light emitted from the phosphor screen as a result of the absorption of x-rays is detected by light sensitive film. The film is then developed to yield an image of the patient's breast which can be viewed on a light box (negatoscope). In digital X-ray systems, a digital X-ray receiver is used on place of the film. The receiver yields an electric signal which can be digitally processed for viewing on a high resolution monitor. Until recently, only limited field of view digital systems, e.g., 5 cm by 5 cm field of view systems, were available, approximating film based systems in mammographic performance. More recently, full-field mammography systems have become available, though at considerable cost mostly due to the high cost of high resolution digital x-ray receivers based on flat panel X-ray detectors.

Heretofore, film-based systems have been most commonly used for breast imaging and improvements over the years in film-based, x-ray imaging technology have resulted in improved imaging capability and reduced radiation dosage. Film based systems are, however, subject to certain limitations. For example, film granularity and random film screen noise limits the spatial resolution of the resulting image. Furthermore, the time required to develop film images renders film-based systems less desirable for some applications, particular where, today, many patients (and physicians) wish to see the results of the diagnostic process immediately.

Recently, researchers have recognized that digital X-ray imaging systems offer potential advantages over film-based imaging systems. Digital mammography systems allow for substantially real-time imaging as may be desired. The stored digital imaging data can also be downloaded for transmission within a computer network and retrieved at remote workstations thereby facilitating information storage, consultation and computer image analysis.

Conventional digital mammography systems based on flat panel receiver have a number of disadvantages. Cost is one major factor—a large-format mammographic X-ray receiver is very expensive and sometimes very sensitive to careless handling and environmental conditions, driving the cost of the overall device and its maintenance costs upwards. Mammography X-ray imaging scanners that use linear matrix (narrow relative to imaging area width) detectors are known (which avoids the use of a very expensive full-field X-ray receiver), which utilize a pendulum-like structure, on which the X-ray detector is mounted, such as described in U.S. Pat. No. 5,526,394. However, such systems suffer from problems associated with flexing and mechanical deformations of the pendulum structure when the X-ray detector base on CCD is moving, which in turn causes a degradation of the image quality. Accordingly, there is a need in the art for a mammography scanner which is low in cost, and provides a high quality digital X-ray image.

SUMMARY OF THE INVENTION

The present invention relates to full field digital mammography, in particular, to an apparatus for X-ray imaging a selected region of a patient's breast by X-ray slot-scanning across the region and constructing a composite transmitting X-ray image of the region based on the scan. The invention has particular application to the field of mammography.

The present invention provides an improved digital mammography apparatus which allows for high resolution, full field breast imaging. In addition, the present invention reduces the effects of scattered radiation without requiring the use of a dose-inefficient grid. The present invention also provides a novel mechanism for acquiring image information as a X-ray detector is scanned across an area of interest and integrating the acquired information to yield a high fidelity composite image of the area of interest. Moreover, the present invention allows for automatic selection of a radiation filter, so that the filter can be selected based on particular X-ray imaging conditions to enhance the resulting image.

In accordance with one aspect of the present invention, an area of interest within a patient's breast is imaged by transmitting a X-ray beam through the patient's breast, scanning an X-ray detector across the area of interest such that the X-ray detector receives the beam over the course of the scan and processing the resulting information to construct a composite breast image. The area of interest may comprise a section of the patient's breast or the entire breast volume. In order to conduct the scan, the slot-scan X-ray beam and the X-ray detector can be synchronously moved across the area of interest. In principle, X-ray beams of various shapes can be utilized, however, beam shapes having a narrow width and a length at least as great as the chest wall-to-nipple length of the patient's breast (e.g., a fan beam) are commonly used.

In order to accurately construct a composite X-ray image based on slot-scan imaging data, it is important to correlate imaging data acquisition to the X-ray detector scanning motion. In accordance with the present invention, this can be accomplished by mounting the vibration dampening mechanism to the pendulum and to the X-ray detector, which reduces vibration of the detector.

In one aspect, there is provided an apparatus for use in X-ray imaging an area of interest within a patient's breast, including a stationary frame; a rotating assembly mounted on the stationary frame, the rotating assembly including an axle assembly having a substantially horizontal axis of rotation (or an axis of rotation orthogonal to a patient's chest wall), an X-ray source that, in one embodiment, has a focal spot that approximately coincides with the horizontal axis of rotation; a collimator from which a fan-shaped X-ray beam exits towards a X-ray detector assembly, and a rotating assembly mechanically coupled to the detector assembly and pivoting about the horizontal axis of rotation. The detector assembly includes a linear X-ray detector for detecting the fan-shaped X-ray beam after the beam passes through the area of interest. The motor is mechanically coupled to the rotating assembly, which in turn bears the detector as well as X-ray tube with collimator attached to it, and enables arcuate movement of the detector assembly in a transverse direction. The motor enables rotational movement of the rotating assembly, and applies a force that is substantially offset from the horizontal axis of rotation. A distance between the detector assembly and the focal spot stays constant throughout the arcuate and rotational movements.

A screw is coupled to the motor and to the rotating assembly (to the rotating assembly), wherein the screw translates rotational force from the motor into the linear movement of a nut along the screw, and then into arcuate movement of the detector. The nut mounted on the screw and a clamp coupled to the nut and slidably coupled to the rotating frame, for enabling rotational movements. The constant distance between X-ray tube focal spot and X-ray detector is enabled by the rigid rotating frame. A first gear is coaxial with the motor and second gear is coaxial with the screw, the first and second gears are coupled by a belt to transfer force from the motor to the screw. The collimator includes an alignment adjustment mechanism. The detector is also rotatable (adjustable) about an axis that is orthogonal to detector surface and to horizontal axis of rotation. A vibration dampening mechanism is coupled to the rotating assembly. The vibration dampening mechanism is mounted on a mounting bracket, and includes a bearing and a spring applying force against the bearing so as to bring the bearing in contact with a fixed plank.

The axle assembly comprises an axle coupled to rotating assembly, the axle rotatable about the horizontal axis of rotation, and two bearings supporting the axle.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE ATTACHED FIGURES

The accompanying drawings, which are included to provide further understanding of the invention and are incorporated in and constitute a part of this specification, illustrate embodiments of the invention and, together with the description, serve to explain the principles of the invention.

Figure 7C:
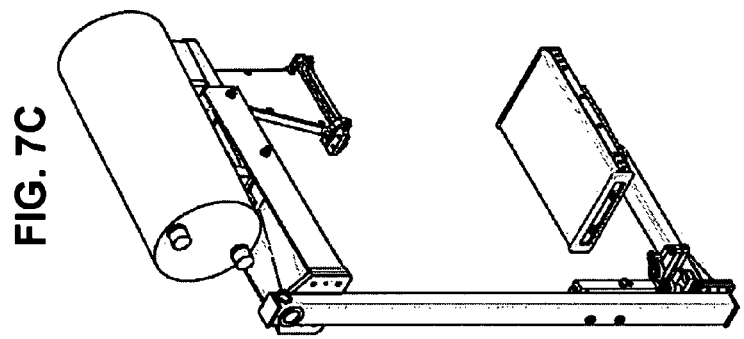
Figure 7A:
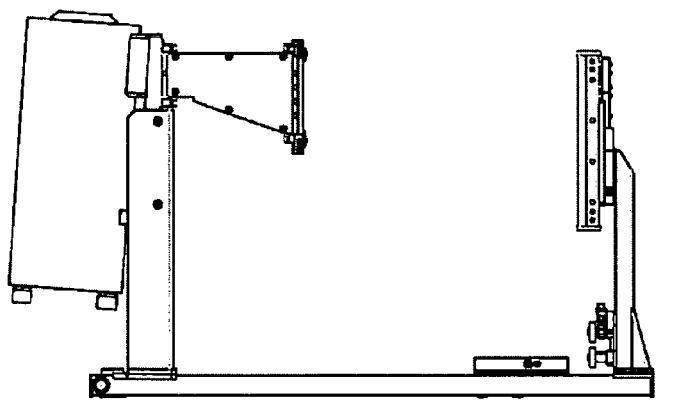
Figure 7B:
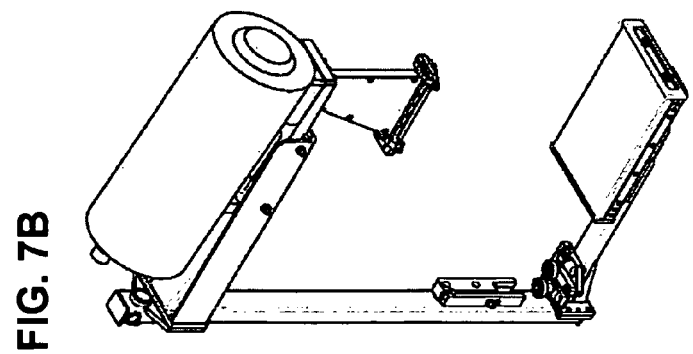

FIGS. 7A-7C provide additional illustrations of the rotating elements.

FIGS. 8A-8D show additional views of the stationary elements.

FIGS. 9A-9D illustrate additional detail of the drive mechanism.

Figure 10B:
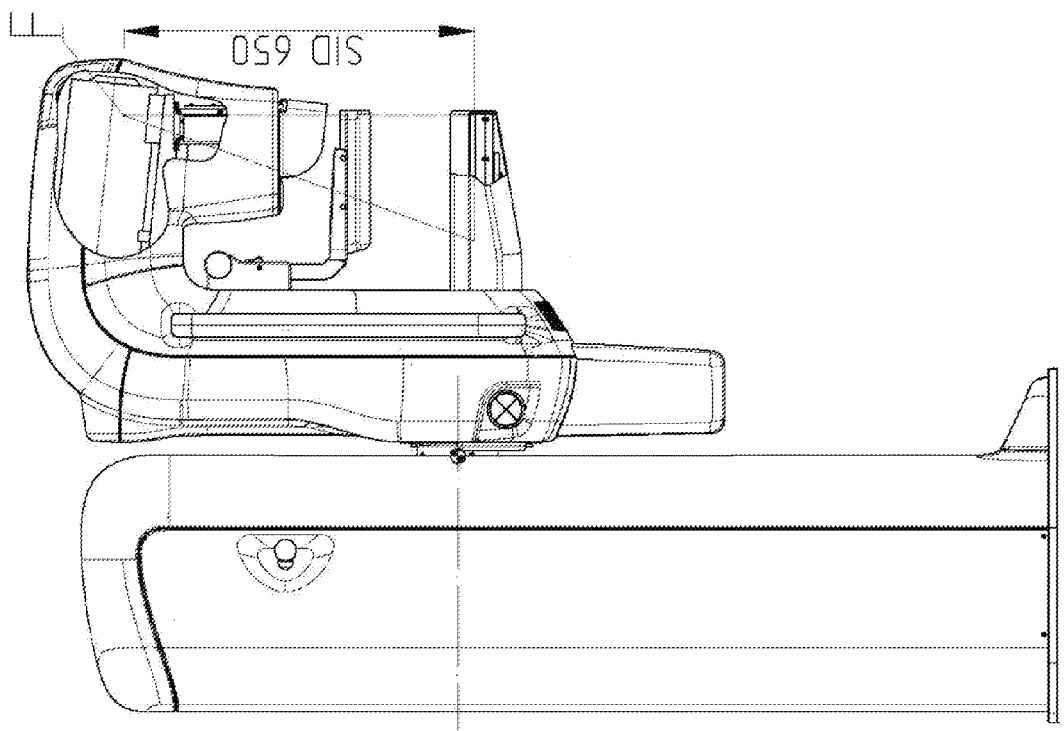
Figure 10A:
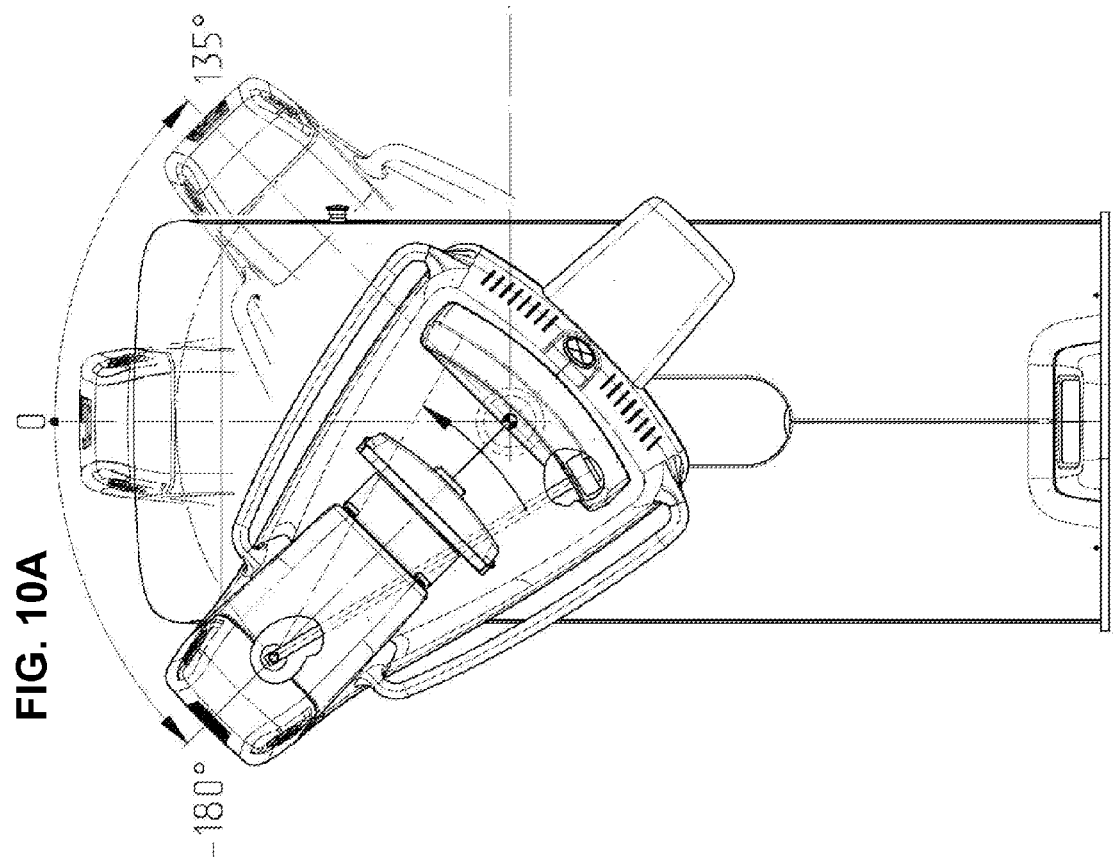

FIGS. 10A-10B illustrate two axes of rotation of the rotating assembly.

DETAILED DESCRIPTION OF THE PREFERRED EMBODIMENTS

Reference will now be made in detail to the preferred embodiment of the present invention, examples of which are illustrated in the accompanying drawings.

The mammography apparatus described herein is a full-field digital mammography system, designed to perform digital X-ray breast imaging for screening and diagnostic purposes (i.e., for early breast cancer detection). The digital full field mammography system is designed to be used in clinical practice to the same purpose, as a traditional analog (film-type) mammographic apparatus. The main features of an exemplary the full-field digital mammography system are (1) digital scanning X-ray image receiver with 54 micron pixel size; and (2) an anti-scatter grid free design, allowing for patient dose reduction with no loss of image quality.

Generally, the digital mammography scanning system uses scanning technology of producing digital X-ray images as follows:

An X-ray image is obtained by scanning of breast with a narrow fan-shaped beam of X-ray radiation;

A projection X-ray image of breast being scanned is detected by a matrix CCD-TDI-based detector with a scintillator, moving synchronously with the X-ray radiation beam;

A digital X-ray image is formed such that a number of image pixels along the scanning direction is determined by the number of scanning steps, and along detector length—by the number of pixels in a single detector column;

special algorithms are used to form and process digital images.

The scanning digital X-ray image receiver allows for low breast radiation dose, high spatial and contrast resolution, reduction of scattered radiation impact on the quality of X-ray image, and high stability to variations of ambient temperature and humidity, including during transportation and storage.

The main components of the digital mammography system are:

(a) Patient stand where X-ray system, comprising X-ray radiation source unit, compression device and digital receiver of X-ray image are mounted, (b) Control console comprising radiation protective screen, (c) Control unit, (d) X-ray generator, (e) Acquisition workstation, (f) Diagnostic workstation (optional).

The mammography imaging process is controlled by programming means from acquisition workstation by specially trained medical personnel (operator). Image review and analysis are performed on special diagnostic workstation equipped with two specialized high-resolution displays.

The digital X-ray image receiver is an important element that includes an X-ray sensitive detector, scanning mechanism, allowing for precision scanning of the imaging area, and electronic controllers. The detector is based on a matrix of light-sensitive elements with scintillation coating built on charge-coupled device technology. Signal at the output of matrix element is proportional to the energy of X-ray photons passing through corresponding breast volume and being subsequently absorbed by scintillator.

The mammogram is formed by scanning a breast with a narrow fan-shaped beam synchronously with detector movement provided by scanning mechanism. In the process of scanning signals from outputs of matrix elements are read one by one, converted in digital form in the control unit and saved as one column of a digital image. Digital image format along scanning direction is determined by respective dimension of the scanned area.

The apparatus can be operated using program-table method of setting exposure parameters, based on automatic changing of anode current and voltage depending on breast thickness in compressed state.

Figure 1:
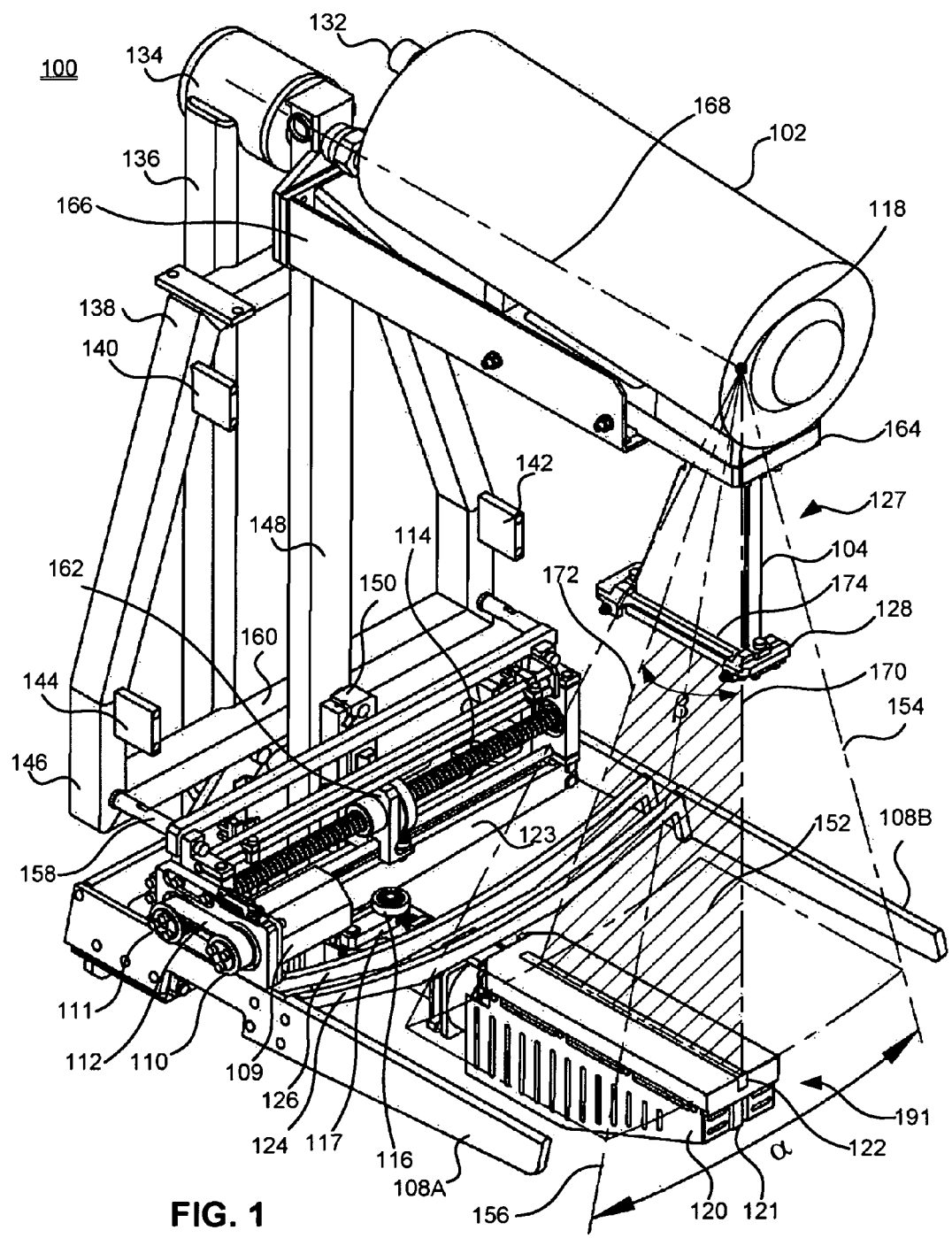
FIG. 1 shows an isometric view of the X-ray swivel-arm system of full field digital mammography scanning system according to one embodiment of the invention.

FIG. 1 illustrates an isometric 3-dimensional view of one embodiment of the invention. As shown in FIG. 1, a digital mammography system 100 includes a frame 136, which is generally fixed, and which serves for mounting the various assembly elements, as will be described below. An X-ray source 102 is positioned generally above the object that is being scanned (i.e., a body part, such as a breast), and typically have the shape illustrated in this figure. Note that the position of the X-ray source can vary depending on the projection of imaging, and it is also possible to arrange the X-ray source below the object. These options can be implemented through rotation of the frame 136 around axle 236 in FIG. 2. 132 designates an attachment, through which cooling fluid, such as high-voltage oil (or, in some cases, water or ethylene glycol), is supplied to the X-ray source 102. A focal spot 118, in FIG. 1, is the point from which the fan-shaped X-ray beam 152 appears to emanate (although note that the beam is not actually fan-shaped until it exits the collimator 127). The focal spot 118 typically coincides with the axis 168, although this is not critical, and some offset (e.g., several millimeters, or perhaps a centimeter or two) is acceptable.

168 designates the axis of rotation of the rotating assembly 290 (see FIG. 2) which is substantially horizontal (or at least horizontal for a system that renders images of patients in the upright position, whereas for a patient who is lying down, the axis would be vertical thus, in the general case, the axis is generally orthogonal to a patient's chest wall), as well as various other auxiliary elements. Element 134 is an axle assembly, whose axis of symmetry coincides with the axis of rotation 168, as will be described further below. Frame elements 138, 136, 146 and 160 can be conceptually viewed as a single element that defines the position of the scanning elements relative to the patient. 148 in FIG. 1 is a pendulum member which is part of a rotating assembly (see additional discussion below) of the digital scan mammography apparatus 100.

A collimator 127 is used to form a fan-shaped X-ray beam. The collimator 127 is comprised of an upper plate 164, a bottom slit portion 174, which includes a slit through which the X-ray beam exits towards the body part being scanned, attachment members 104, and a beam alignment element 128, all of which, collectively, serve as a collimator 127 and produce a fan-shaped beam 152, as illustrated in the figure. The fan-shaped beam 152 forms an angle β (typically, about 20 degrees) between its boundaries 172 and 170. The beam also scans laterally (i.e., left to right and/or vice versa in FIG. 1), generally through the angle α (typically, about 25 degrees or at least large enough to scan an image of approximately 30 cm wide), which is defined by the outermost swings of the beam 152, designated by 156 and 154.

Generally, the collimator 127 is made of material that is opaque to x-rays, such as steel with a lead coating inside. The collimator 127 works in two stages, first producing a "rough" beam, which is then used by the alignment element 128, to form the final fan-shaped beam 152.

Brackets 140, 144 and 142 are attached to the frame members 138, 146, and are used to mount a breast compression device, which will be further described with reference to FIG. 2.

Also shown in FIG. 1 is a detector assembly 191, comprising a linear CCD-based X-ray sensor 122, a shield 120, all of which are mounted on a support 121. The detector assembly 191 moves arcuately back and forth (i.e., transverse to the chest wall), in alignment with the X-ray beam 152, as the X-ray beam is scanned across a patient's body part. The movement of the detector assembly 191 is effected by a stepper motor 109, which rotates a gear 110. The gear 110 translates the force from the motor 109 to a belt 112, and then to a gear 111. The gear 111 then rotates a screw 114. A nut 162, to which the detector assembly 191 is attached, moves linearly along the screw back and forth (left to right, or right to left, in FIG. 1), due to the rotation of the motor 109.

As will be appreciated, when the rotating assembly 290 rotates about the axis 168, the distance between the axis 168 and the nut 162 changes as the nut 162 travels along the screw 114. In order to enable the rotating assembly 290 to rotate, the distance at which the nut 162 is located, relative to the axis 168, needs to change as well. This is done using a fork/clamp 150, as will be further explained with reference to FIG. 4.

Also in this figure are shown a horizontal connecting member 160 that connects the left and right halves of the frame 138, 146, and a spacer/joint 158 for mounting the coordinate table at an offset. The term "coordinate table" refers to the assembly of the nut 162, the screw 114, the gears 110, 111, the belt 112, the motor 109, and other related elements, since any position of the nut on the screw can be described in terms of the steps of the motor, which in turn translates into a coordinate of nut position relative to the starting position of the nut on the screw 114.

Additionally, on either side of the detector assembly 191 are rails 108A, 108B that are used to mount patient table supporting a breast during examination. The rails are connected using connecting members 124, 126, to reduce or prevent vibration and twisting of the rails 108A, 108B, thereby providing additional rigidity to the overall system.

Figure 3:
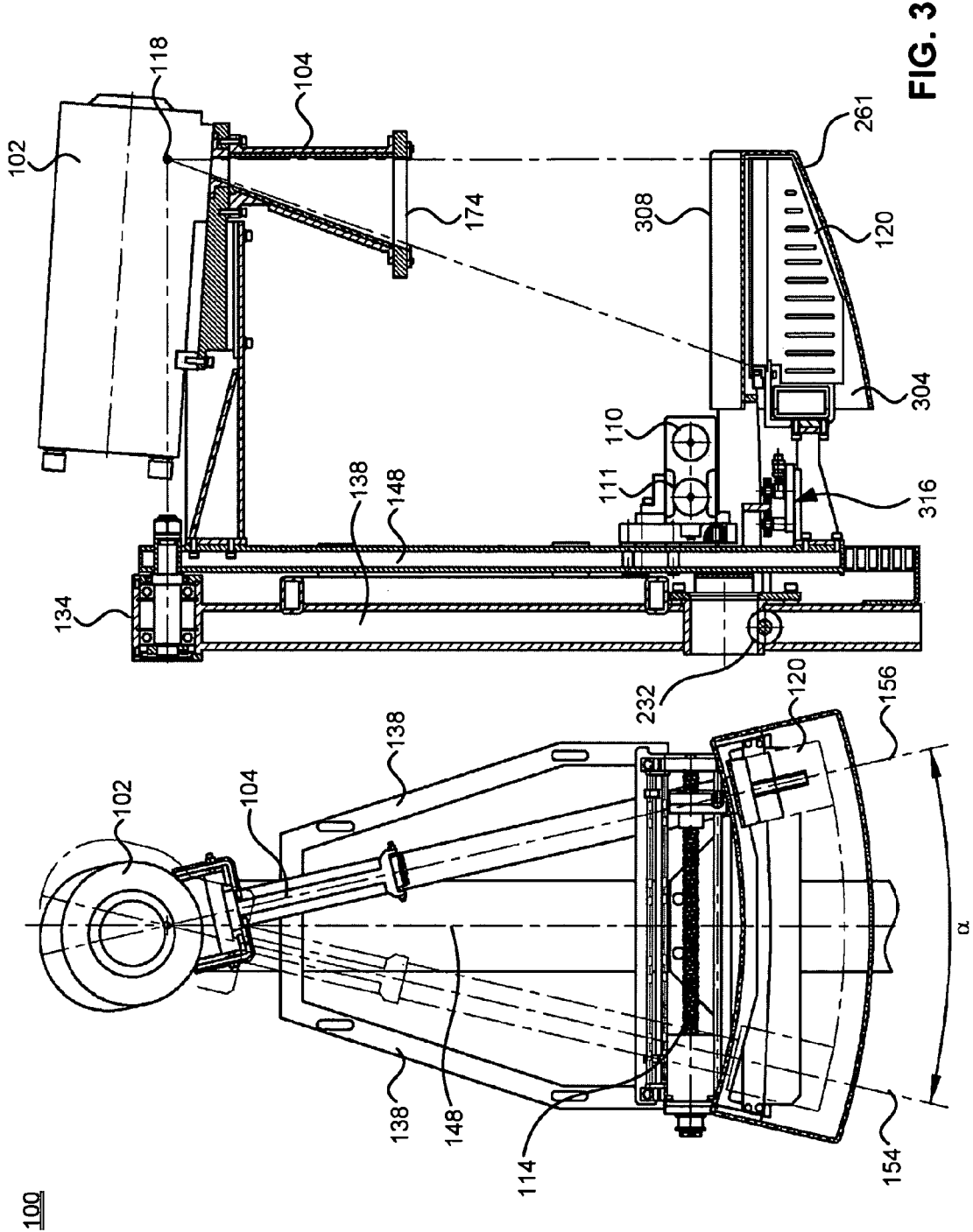
FIG. 3 shows the front view and the side view of the X-ray swivel-arm system of the digital mammography system without a compression device.
Figure 4:
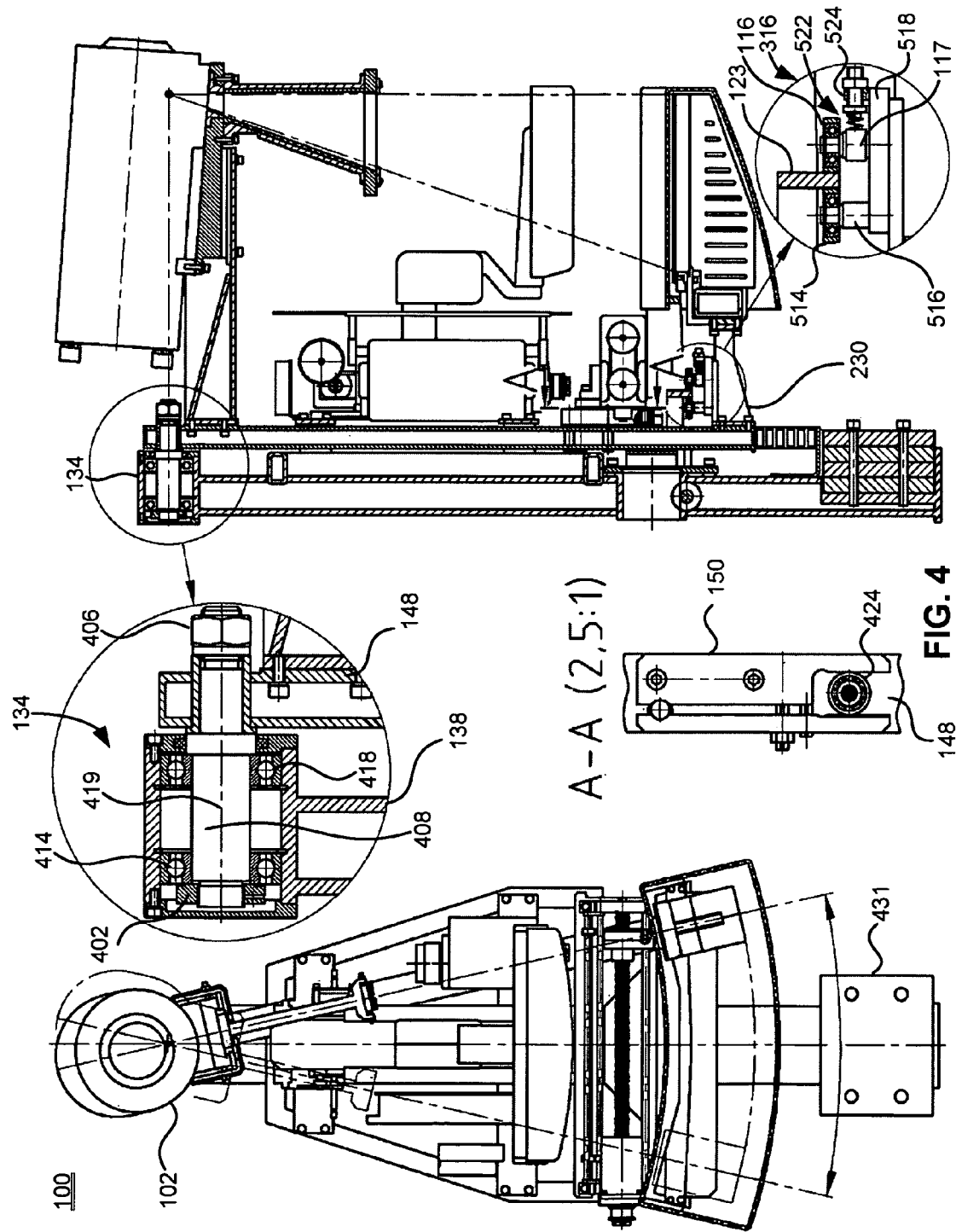
FIG. 4 shows additional detail of several elements of the digital mammography system.

Additionally, in order to reduce vibration, a vibration dampening mechanism 316 is used, including a plank 123, and a lever 117, and a roller 116 (see also FIG. 3), which will also be described with more detail with reference to FIG. 4.

The clamp 150 permits the nut 162 to slide along the pendulum member 148 as the rotating assembly 290 rotates. Thus, the distance between the sensor 122 and the X-ray source 102 stays constant as the detector assembly 191 moves further from the central position, however, as will be appreciated, without giving the nut 162 freedom to move along pendulum member 148, the rotating assembly 290 will be unable to rotate. As will be appreciated, elements 134, 136, 138, 140, 144, 146, 160 form a single welded frame that rotates (tilts) about the axle 236, so that a patient breast can be imaged in different projections, without having to move the patient. (See illustration in FIGS. 10A, 10B.) Elements 102, 240, 242, 148, 230, 191, which are part of the rotating assembly 290, form a quasi-pendulum, and which rotates about a pivot axis 168 during the scanning process (where the pendulum rotates back after a breast scan is completed).

As will be further appreciated, the motor 109, gears 110, 111 and belt 112 are not the only possible mechanism for rotating the screw 114. As an alternative, the motor 109 can drive the screw 114 directly. As another alternative, the motor 109 can rotate the gear 110, which will then directly rotate the gear 111 (without the belt 112). Other options include orienting the motor 109 along the vertical axis, and use a worm gear or similar mechanism to transfer the rotational force to the screw 114. However, it is believed that the mechanism illustrated in FIG. 1 is optimal, both in terms of reducing the overall dimensions and footprint of the device 100, as well as in terms of reducing mechanical vibrations that are transmitted from the motor 109 to the rest of the rotating and moving mechanisms. Other mechanisms for moving the detector assembly in an arcuate manner (generally left to right) can include, for example, linear motors.

Figure 2:
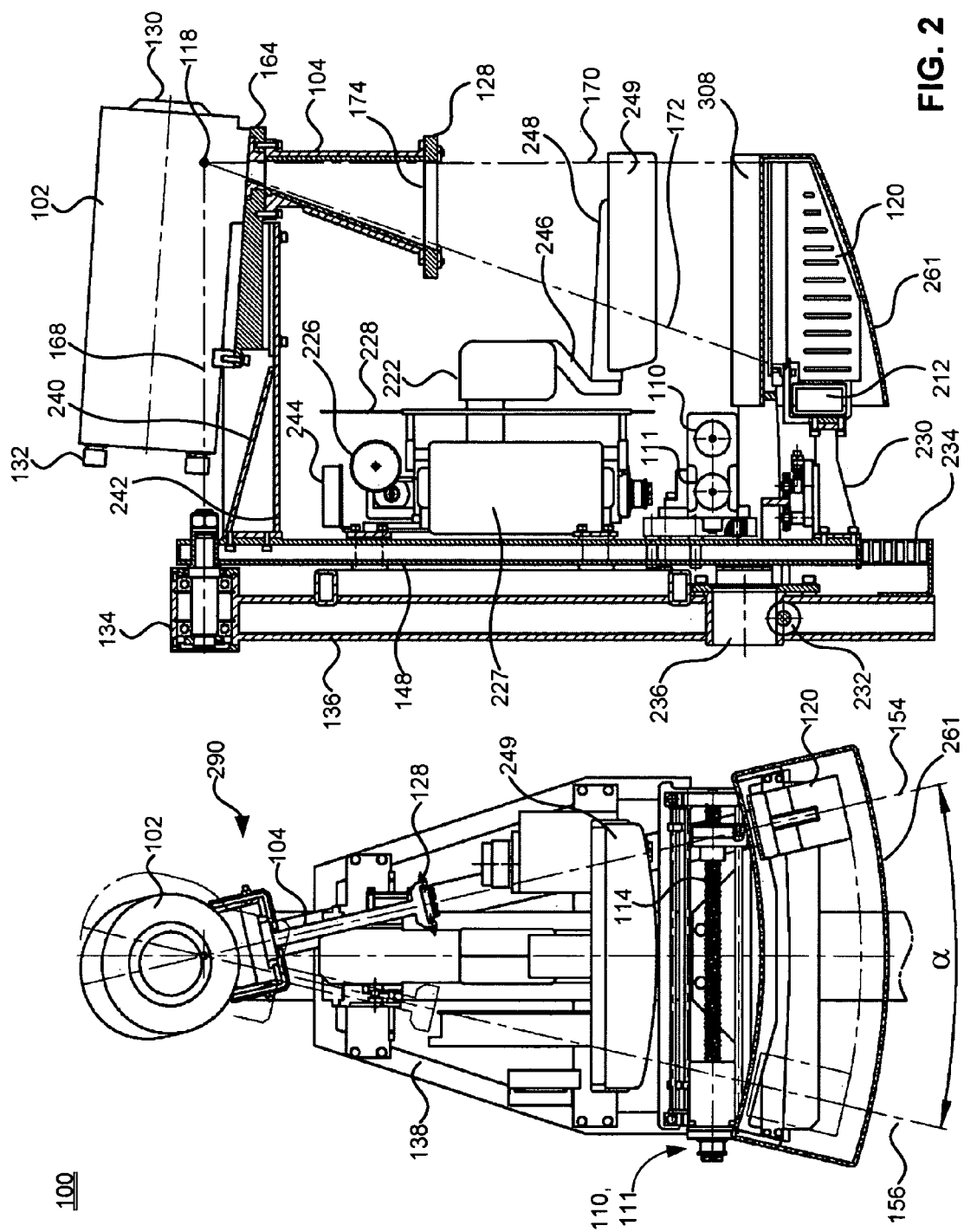
FIG. 2 shows a front view and a side view of the X-ray swivel-arm system of the digital mammography system.

FIG. 2 illustrates two additional views of the digital scan mammography apparatus 100, according to one embodiment of the invention. Shown in FIG. 2 are a front view of the digital scan mammography apparatus 100 on the left, and a side view of the digital scan mammography apparatus 100 on the right. As further shown in FIG. 2, the mammography unit includes a support bracket 242, 240, used to support the X-ray source 102.

Also shown in FIG. 2 is a mounting bracket 230, used to support the detector assembly 191. The mounting bracket 230 is a part of pendulum and is attached to pendulum member 148 (see also FIGS. 7A-7C). Both brackets 240 and 230 are rigidly connected to pendulum member 148. A height adjustment mechanism, which is not shown in the figures, moves the axle 236 up and down, to the digital scan mammography apparatus 100 to move up and down, to adjust for the patient's height (note that the drive for moving the digital scan mammography apparatus 100 up and down is not shown in the drawings). A cable bundle is connected to the detector assembly 191, using a belt 234. Also, 212 is a cooling assembly for the detector assembly 191.

In FIG. 2, 232 is a lock that fixes welded stationary frame together with rotating assembly 290 to the axle 236 and permits the detector assembly 191 and the rotating assembly 290 and the breast compression device (described below) to both move up and down and to tilt plus/minus 90° (in this exemplary embodiment), as viewed from the patient's perspective. This permits easier use of the digital scan mammography apparatus by the physician and the patient and permits scans of different areas from different angles for patients having different heights.

Also shown in FIG. 2 is a breast compression device, comprising a paddle 249, a holding bracket 248, a mounting bracket 246, a tension meter (measurement device) 222, used to measure the compression force value (to ensure that the compression force is a defined value, for example, compression force around 15 kilograms is often preferred), a distance measurement mechanism 226, and a control block for the breast compression device 227. 228 is a cover of the aperture for compression device movement. Note that the paddle 249 with its holding bracket 248 and mounting bracket 246 are replaceable, and generally cup shaped. Different sizes of the paddle assembly 249 can be provided. Holding brackets 248 of different sizes are used to attach the paddles of different size.

FIG. 3 is another view of the digital scan mammography apparatus without the compression device, with the front view shown on the left, and a side view shown on the right. Note also an X-ray-transparent cover 261, which is typically made from plastic or similar material. Also, 316 in FIG. 3 designates a vibration dampening mechanism, which will be described further with reference to FIG. 4.

Figure 5:
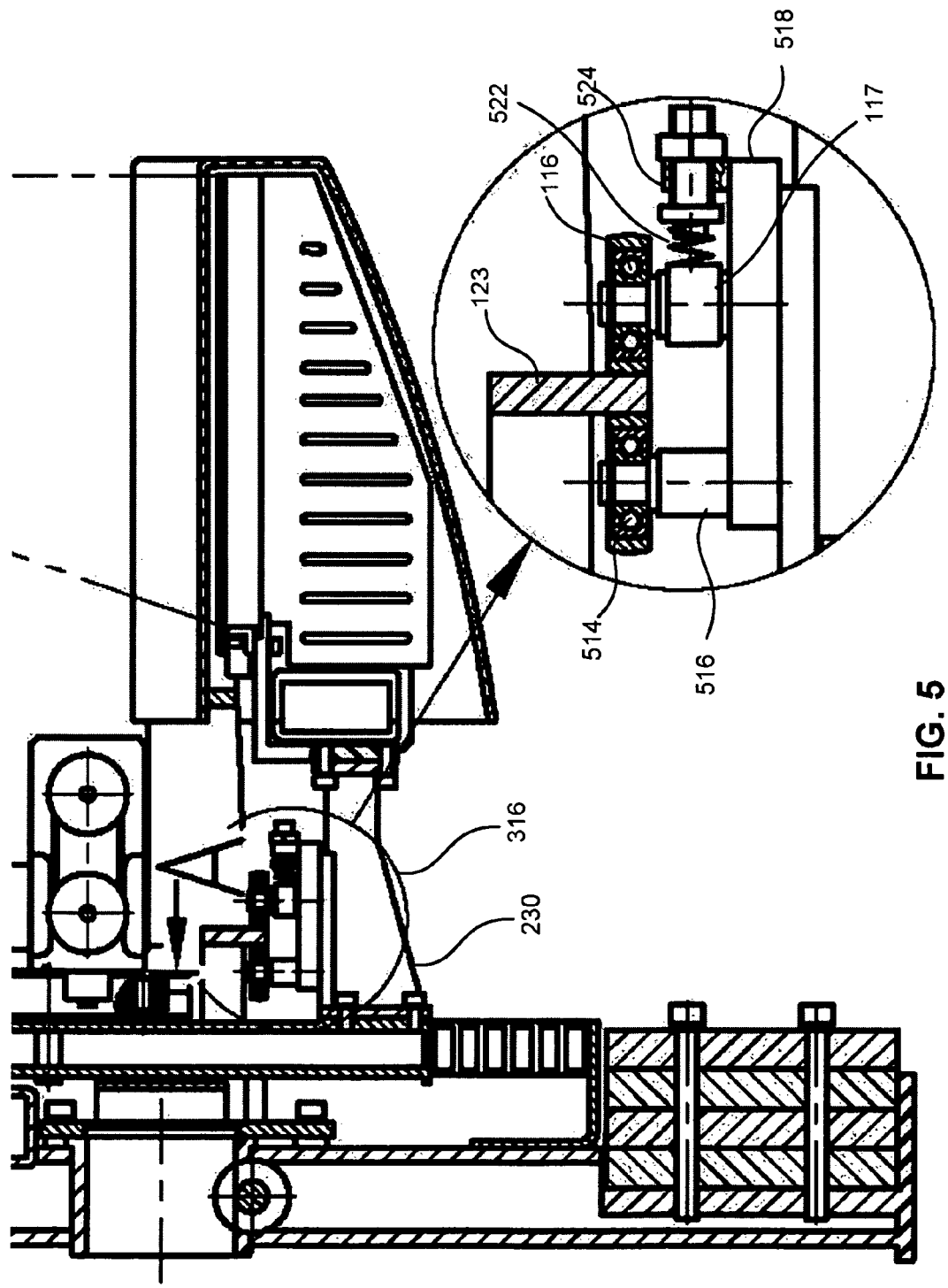
FIG. 5 is an expanded view of the vibration dampening mechanism shown in FIG. 4.

FIG. 4 illustrates additional detail of several of the elements of the digital scan mammography apparatus 100. As shown in FIG. 4, on the lower right, and a larger view in FIG. 5, the vibration dampening device 316 is mounted on the bracket 230. The vibration dampening device 316 includes two bearings, 514 and 116, which are mounted on axles 516 and 117, respectively. The bearings 516, 116 are on either side of the plank 123. A spring 522, which is attached to a mounting member 524, exerts a force against the lever 117, which makes the detector assembly 191 follow the plank 123, thereby reducing vibration. The vibration dampening mechanism 316 is mounted on a base 518, which is attached to the bracket 230.

Also shown in FIG. 4 is additional detail of the axle assembly 134, which is used as a pivot around which the rotating assembly 290 rotates. The axle assembly 134 includes an axle 408, whose axis coincides with the axis of rotation 168. Two bearings 414, 418, are used to enable rotation of the axle 408. A front nut 406, and a rear nut 402 are used to fix the position of the various elements, the axle 408 and other elements of the rotating assembly 290, relative to reach other.

Also shown in FIG. 4 is additional detail of the clamp 150, which is used to enable movement of the detector assembly 191 up and down during the detector assembly 191's movement in the lateral directions (together with rotation of the assembly 290 around the axis 168). A bearing 424 moves along clamp 150 that is attached to pendulum member 148 to permit the bearing's 424 slidable movement in the vertical direction. As such, when the motor 109 imparts rotational motion to the wheel 110, which is transmitted to the wheel 111, and is in turn transmitted to the screw 114, the nut 162 moves left to right in FIG. 1, and, as the rotating assembly 290 rotates, the distance between the detector assembly 191 and the X-ray source 102 stays the same, however, the height of the detector assembly 191 changes, due to the slidable motion of the mechanism shown in the center of FIG. 4.

Note also that in FIG. 4, on the left side, the front view is generally similar to the view shown in FIG. 2, with the added counterweight 431. The counterweight 431 is generally used to ensure more secure placement of the overall digital scan mammography apparatus 100 and to reduce power of the rotating motor, particularly given the fact that various elements and assemblies can both rotate about various axes and move up and down.

Figure 6:
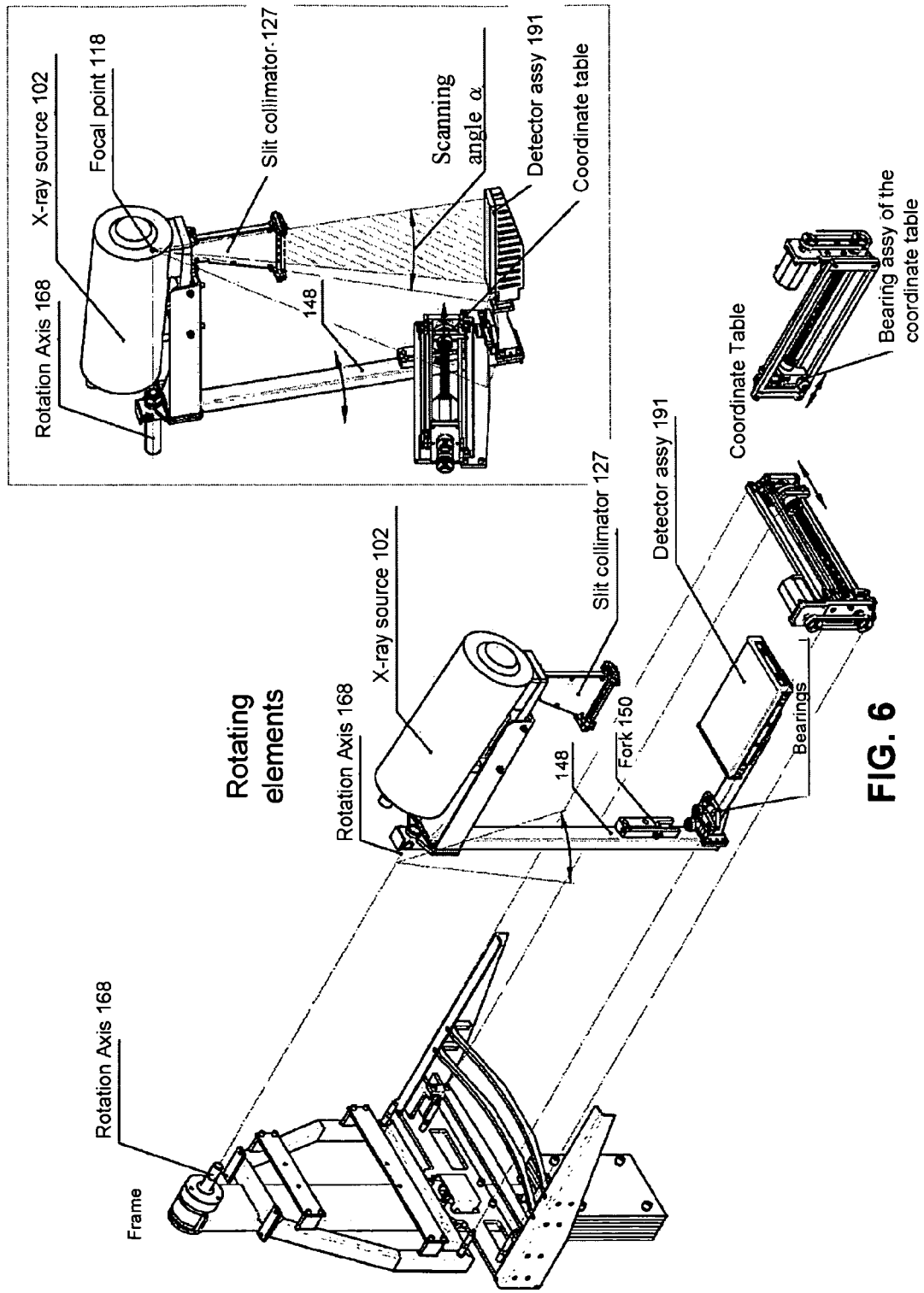
FIG. 6 illustrates an exploded view of the frame and the rotating elements.

FIGS. 6-9 illustrated additional detail of the digital scan mammography apparatus 100 of the present invention. FIG. 6 illustrates an exploded view of the frame and the rotating elements, specifically, the pendulum portion of the digital scan mammography apparatus, which includes the x-ray source, the pendulum member 148, the fork 150 and the detector assembly 191. A side view, in the upper right, is also shown.

FIGS. 7A-7C provides additional illustrations of the rotating elements. FIG. 7A shows a side view of the pendulum and FIGS. 7B and 7C illustrate two isometric views of the same.

Figure 8D:
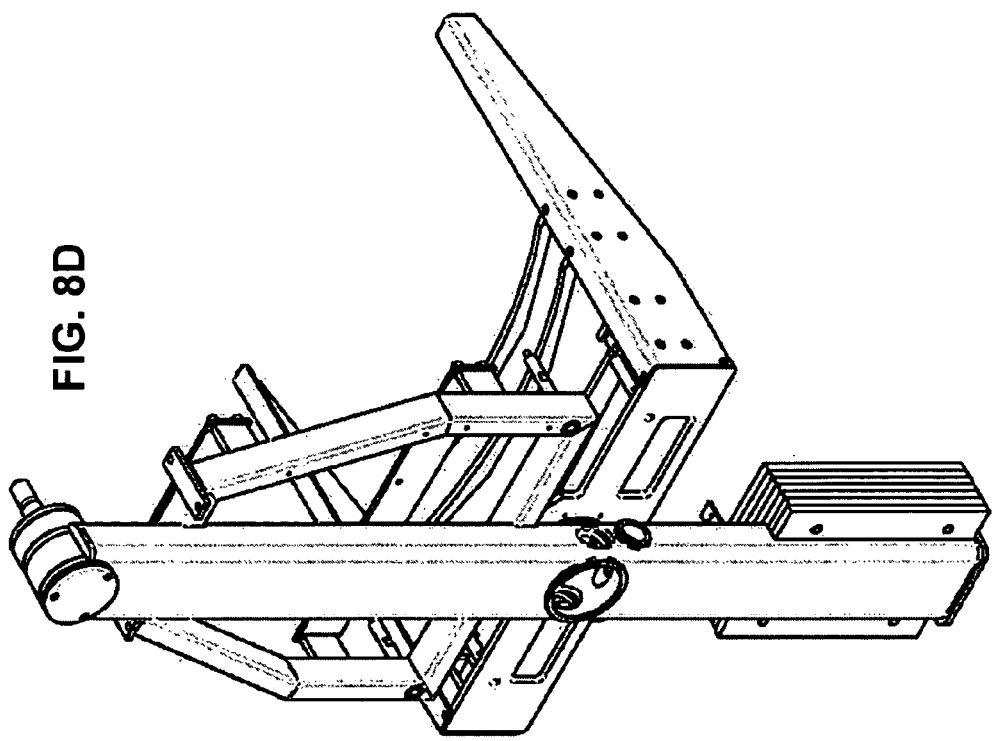
Figure 8C:
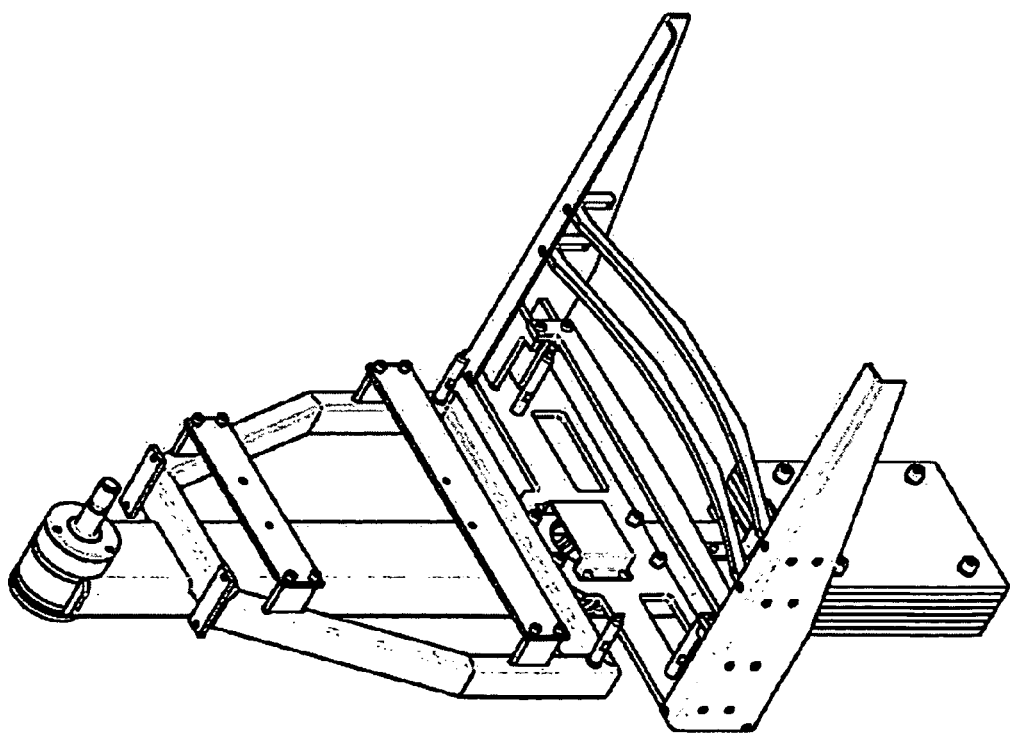

FIGS. 8A-8D show additional views of the stationary elements. FIG. 8A shows a front view, and FIG. 8B shows a side view. FIGS. 8C and 8D illustrate two isometric views of the same, from two different angles.

Figure 9B:
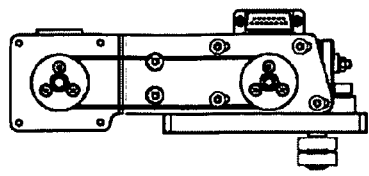
Figure 9D:
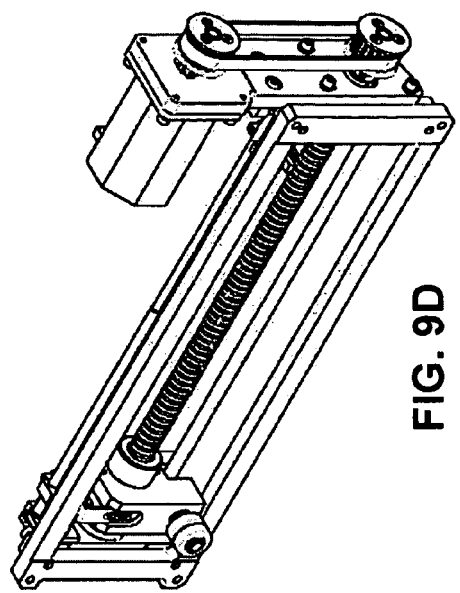
Figure 9A:
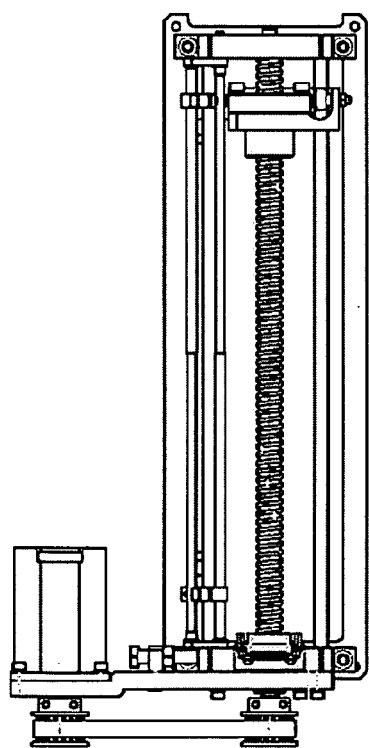
Figure 9C:
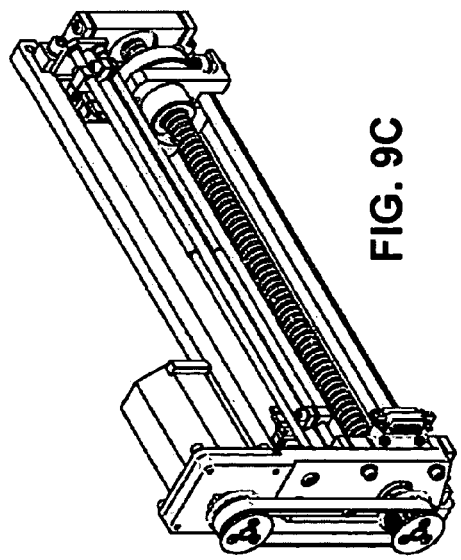

FIGS. 9A-9D illustrates additional detail of the drive mechanism. FIG. 9A shows a front view (note the screw, oriented left to right), and FIG. 9B shows a side view. FIGS. 9C and 9D illustrate additional isometric views, where the arrangement of the motor relative to the screw and how the force of the motor is transmitted, is shown.

Having thus described a preferred embodiment, it should be apparent to those skilled in the art that certain advantages of the described method and apparatus can be achieved. It should also be appreciated that various modifications, adaptations and alternative embodiments thereof may be made within the scope and spirit of the present invention. The invention is further defined by the following claims.

What is claimed is:

1. An apparatus for use in imaging an area of interest within a patient's breast, comprising:
    a stationary frame;
    a rotating assembly mounted on the stationary frame, the rotating assembly including
    an axle assembly having a first axis of rotation that is orthogonal to a patient's chest wall,
    a collimator from which a fan-shaped X-ray beam exits towards a detector assembly, and
    a rotating frame carrying the detector assembly and pivoting about the first axis of rotation;
    the detector assembly comprising a linear X-ray detector for detecting the fan-shaped X-ray beam after the beam passes through the area of interest;
    the rotating assembly being mechanically coupled to a motor that enables arcuate movement of the detector assembly in a transverse direction;
    the motor enabling rotational movement of the rotating assembly by driving the rotating assembly and applying a force at a location offset from the first axis of rotation,
    wherein the arcuate movement and the rotational movement are synchronized, and
    further comprising a screw coupled to the motor and to the rotating assembly, wherein the screw translates rotational force from the motor into the arcuate movement of the detector.

2. The apparatus of claim 1, wherein the collimator includes an alignment adjustment mechanism.

3. The apparatus of claim 1, further comprising a vibration dampening mechanism coupled to the detector assembly.

4. The apparatus of claim 3, wherein the detector assembly is mounted on a mounting bracket, the vibration dampening mechanism is mounted on the mounting bracket, and the vibration dampening mechanism comprises a bearing and a spring applying force against the bearing so as to bring the bearing in contact with a fixed plank.

5. An apparatus for use in imaging an area of interest within a patient's breast, comprising:
    a stationary frame;
    a rotating assembly mounted on the stationary frame, the rotating assembly including
    an axle assembly having a first axis of rotation that is orthogonal to a patient's chest wall,
    a collimator from which a fan-shaped X-ray beam exits towards a detector assembly, and
    a rotating frame carrying the detector assembly and pivoting about the first axis of rotation;
    the detector assembly comprising a linear X-ray detector for detecting the fan-shaped X-ray beam after the beam passes through the area of interest;
    the rotating assembly being mechanically coupled to a motor that enables arcuate movement of the detector assembly in a transverse direction;
    the motor enabling rotational movement of the rotating assembly by driving the rotating assembly and applying a force at a location offset from the first axis of rotation,
    wherein the arcuate movement and the rotational movement are synchronized;
    a nut mounted on the screw and a clamp coupled to the rotating frame, for translating a linear movement of the nut into the arcuate and rotational movements; and
    a first gear coaxial with the motor and second gear coaxial with the screw, the first and second gears coupled by a belt to transfer force from the motor to the screw.

6. An apparatus for use in imaging an area of interest within a patient's breast, comprising:
    a stationary frame;
    a rotating assembly mounted on the stationary frame, the rotating assembly including
    an axle assembly having a first axis of rotation that is orthogonal to a patient's chest wall,
    a collimator from which a fan-shaped X-ray beam exits towards a detector assembly, and
    a rotating frame carrying the detector assembly and pivoting about the first axis of rotation;
    the detector assembly comprising a linear X-ray detector for detecting the fan-shaped X-ray beam after the beam passes through the area of interest;
    the rotating assembly being mechanically coupled to a motor that enables arcuate movement of the detector assembly in a transverse direction;
    the motor enabling rotational movement of the rotating assembly by driving the rotating assembly and applying a force at a location offset from the first axis of rotation,
    wherein the arcuate movement and the rotational movement are synchronized, and
    wherein the rotating assembly is also rotatable about a second axis.

7. An apparatus for use in imaging an area of interest within a patient's breast, comprising:
    a stationary frame;
    a rotating assembly mounted on the stationary frame, the rotating assembly including
    an axle assembly having a first axis of rotation that is orthogonal to a patient's chest wall,
    a collimator from which a fan-shaped X-ray beam exits towards a detector assembly, and
    a rotating frame carrying the detector assembly and pivoting about the first axis of rotation;
    the detector assembly comprising a linear X-ray detector for detecting the fan-shaped X-ray beam after the beam passes through the area of interest;
    the rotating assembly being mechanically coupled to a motor that enables arcuate movement of the detector assembly in a transverse direction;
    the motor enabling rotational movement of the rotating assembly by driving the rotating assembly and applying a force at a location offset from the first axis of rotation,
    wherein the arcuate movement and the rotational movement are synchronized, and
    wherein the axle assembly comprises an axle coupled to the X-ray collimator source, the axle rotatable about the first axis of rotation, and two bearings supporting the axle.

8. An apparatus for use in imaging an area of interest within a patient's body, comprising:
    a frame having a stationary portion and a rotating portion, the rotating portion having a first axis of rotation substantially orthogonal to a patient's chest wall,
    an X-ray source coupled to the rotating portion and emitting a fan-shaped X-ray beam;

a linear X-ray detector for detecting radiation of the fan-shaped X-ray beam after the beam passes through the area of interest;

the linear X-ray detector being movable arcuately in a transverse direction in synchronization with rotational movement of the rotating portion and the X-ray source;

a motor coupled to the linear X-ray detector to enable the arcuate movement and coupled to the rotating portion to enable the rotational movement of the rotating portion, wherein the motor applies a force at a location offset from the first axis of rotation; and a screw coupled to the motor and to the rotating portion, wherein the screw translates rotational force from the motor into the arcuate movement of the detector.

9. The apparatus of claim 8, further comprising a nut mounted on the screw and a clamp coupled to the rotating portion frame, for translating a linear movement of the nut into the arcuate and rotational movements.

10. The apparatus of claim 9, further comprising a first gear coaxial with the motor and second gear coaxial with the screw, the first and second gears coupled by a belt to transfer force from the motor to the screw.

11. The apparatus of claim 8, wherein the rotating portion and the detector are also rotatable about a second axis.

12. The apparatus of claim 8, further comprising a vibration dampening mechanism coupled to the detector assembly.

13. The apparatus of claim 12, wherein the detector is mounted on a mounting bracket, the vibration dampening mechanism is also mounted on the mounting bracket, and the vibration dampening mechanism comprises a bearing and a spring applying force against the bearing so as to bring the bearing in contact with a fixed plank.

14. A method for imaging an area of interest within a patient's body, the method comprising:

rotating a rotating assembly about a substantially horizontal axis of rotation, the rotating assembly including an axle assembly whose axis is coincident with the horizontal axis, an X-ray source having a focal spot that coincides with the horizontal axis of rotation, a collimator from which a fan-shaped X-ray beam exits towards a detector assembly, and a rotating frame mechanically coupled to the detector assembly and pivoting about the horizontal axis of rotation;

emitting a fan-shaped X-ray beam from the X-ray source towards the detector assembly;

applying a force to a linear X-ray detector that is mounted on the detector assembly at a location offset from the horizontal axis of rotation;

moving the detector assembly arcuately in a transverse direction in synchronization with rotational movement of the rotating assembly and the X-ray source so as to maintain constant a distance between the linear X-ray detector and the X-ray source as the X-ray detector moves arcuately and the X-ray source rotates; and detecting radiation of the X-ray beam after the beam passes through the area of interest.

\* \* \* \* \*